United States Patent [19]

Castro et al.

[11] Patent Number: 4,886,914

[45] Date of Patent: Dec. 12, 1989

[54] PROCESS FOR SYNTHESIS OF ALPHA AKLYL AMINO ALDEHYDES

[75] Inventors: Bertrand Castro, Perols; Jean Fehrentz, Montpellier, both of France

[73] Assignee: Sanofi, Paris, France

[21] Appl. No.: 760,524

[22] Filed: Jul. 30, 1985

Related U.S. Application Data

[63] Continuation of Ser. No. 516,709, Jul. 25, 1983, abandoned.

[30] Foreign Application Priority Data

Jul. 30, 1982 [FR] France .................................. 82 13385

[51] Int. Cl.$^4$ .............................................. C07C 95/08
[52] U.S. Cl. .................... 564/343; 564/302; 564/340; 564/402
[58] Field of Search ................ 260/453 RN; 564/138, 564/340, 402, 343

[56] References Cited

U.S. PATENT DOCUMENTS 3,027,407  3/1962  Major et al. ................. 260/453 RN
3,166,589  1/1965  Richter ........................ 260/453 RN
3,280,226 10/1966  Barnas et al. ................ 260/453 RN
3,726,881  4/1973  Kispaludy et al. ........... 260/453 RN

OTHER PUBLICATIONS

Millar et al., "Sidgwick's Organic Chemistry of Nitrogen", 3rd Ed., pp. 333–337 (1966).
Patai, "The Chemistry of Functional Groups, The Chemistry of the Carbonyl Group", pp. 221–225 (1966).
Stanfield et al., "Journal Organic Chemistry", vol. 46, No. 23, pp. 4797–4798 (1981).

Primary Examiner—Robert V. Hines
Attorney, Agent, or Firm—Bacon & Thomas

[57] ABSTRACT

The present invention relates to a process for the preparation of alpha alkyl amino aldehydes of formula

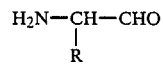

in which R is alkyl or aralkyl possibly substituted, characterized in that N,O-dimethylhydroxylamine is reacted, in a basic medium, on a blocked amine ester of an amino acid of formula

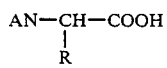

and in that the product obtained is reduced with the aid of a hydride such as the double hydride of lithium-aluminum.

12 Claims, No Drawings

PROCESS FOR SYNTHESIS OF ALPHA AKLYL AMINO ALDEHYDES

This application is a continuation of application Ser. No. 516,709, filed July 25, 1983, and now abandoned.

The present invention relates to a process for synthesis of alpha alkyl amino aldehydes.

The alpha alkyl amino aldehyde family is particularly interesting both as regards the therapeutical properties of these compounds and as regards the possibility of using them as intermediate of synthesis.

However, the synthesis of such compounds is delicate when it is question of chiral molecules mainly by reason of the very easy racemization of the assymmetrical carbon of the molecule.

Up to the present time, the preparation of α alkyl amino aldehydes resulted either from the reduction of the corresponding α amino acids or α amino esters, or from the oxidation of the corresponding alcohols.

In any case, the fairly low yields necessitated more or less laborious purifications and the racemization of the products remained a major problem leading to products of very low rotatory power (cf. in particular Journal of Organic Chemistry 46, 4749, (1981)).

It is an object of the present invention to provide a new method for preparing α alkyl amino aldehydes which avoid the phenomena of recemization and lead, with a good yield, to obtaining α alkyl amino aldehydes presenting a high rotatory power.

This process is summarized in the following reaction scheme:

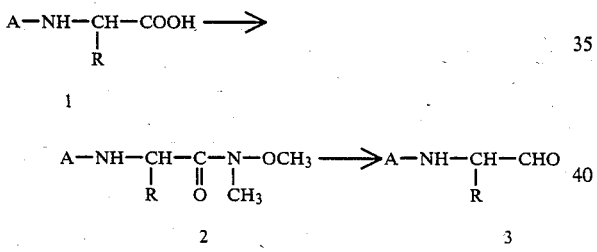

wherein A represents a group capable of reversibly blocking the amine function.

The starting product is the α amino acid

in which R is a straight or branched alkyl group, or an aralkyl group possibly substituted by one or more hydroxy, thiol or NH—R' groups, R' being an atom of hydrogen or an alkyl radical. In particular, R may represent the side chain of the natural α amino acids.

In order to avoid any parasitic intra- or inter-molecular reaction in the course of preparation of the amino aldehydes, it is necessary previously to block the amine function. An acyl group such as the t-butoxycarbonyl (BOC) group is advantageously used.

Similarly, when the side chain R comprises reactive substituents, it is necessary previously to block said substituents. The groups generally used in peptide synthesis may be employed to this end, particularly benzyl ether.

The first step of synthesis consists in preparing the N-methoxy N-methylamides 2 by action of N,O-dimethylhydroxylamine on an activated ester of aminoacid 1. The activated ester is prepared in situ within an appropriate solvent such as methylene chloride or ethyl acetate by a method known per se, then without isolation by the addition of N,O-dimethylhydroxylamine in a basic medium, products 2 are obtained. Products 2 are generally in the form of oils; they are very stable and may be conserved without apparent decomposition.

The second step consists in reducing the N-methoxy N-methylamides 2 thus obtained by a double hydride and preferably the hydride of lithium-aluminium in excess.

Operation is carried out at low temperature, preferably at 0° C. within an appropriate solvent such as ether or tetrahydrofuran.

After isolation, the α alkyl amino aldehydes are obtained with a high yield. They are most often in the form of oil of satisfactory purity.

They present a high rotatory power, contrary to the products described in the prior art.

The invention will be more readily understood on reading the following non-limiting examples.

For greater simplicity, the following abbreviations will be used in the following description:

Leu=Leucine
Boc=tert-butoxycarbonyl

The NMR spectra were recorded at 250 MHz in solution in deuterochloroform, the internal reference being tetramethylsilane.

The following abbreviations were used:
s=singlet
d=doublet
t=triplet
q=quadruplet
m=massive
J-represents the coupling constant expressed in Hertz.

EXAMPLE 1

2-(tert-butoxycarbonylamino) 4-methyl pentanal

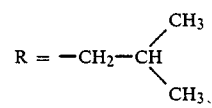

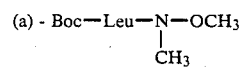

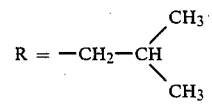

To 2.15 g of L-Boc Leucine dissolved in 50 ml of methylene chloride, are added 1.3 g of diisopropyl ethylamine and 4.26 g of hexafluorophosphate of N-benzotriazolyloxy tris dimethylamino phosphonium. 1.07 g of hydrochloride of N,O-dimethylhydroxylamine and 1.42 g of diisopropylethylamine are then added and left with stirring.

The reaction is followed by thin layer chromatography of a sample. When the reaction is complete (30 to 60 minutes), methylene chloride is added and the solution is washed successively with a 3N hydrochloric acid solution then with a saturated solution of sodium bicarbonate and finally with a saturated solution of sodium chloride.

The solution is dried over magnesium sulphate and the solvent is evaporated to dryness in vacuo. The oily residue is chromatographed over silica to yield a colourless viscous oil.

Yield 94%

$\alpha_D^{20} = -22.7°$ (c=1% methanol)

NMR spectrum:

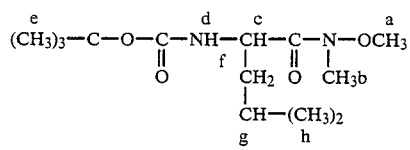

1H at 5.32 ppm ($H_d$, d, $J_{dc}=7.5$)-1H at 4.73 ppm ($H_c$, dt, $J_{cd}=7.5$)-3H at 3.79 ppm ($H_a$, S)-3H at 3.19 ppm ($H_b$, S)-1H at 1.81-1.65 ppm ($H_g$, m) 2H at 1.52-1.30 ppm ($H_f$, m)-9H at 1.44 ppm ($H_e$, S)-6H at 0.95 ppm ($H_h$, 2d, $J_{hg}=6.5$).

(b) -Boc-Leu-H

To a solution of 1.1 g of the amide obtained hereinabove in 40 ml of ether, are added, at 0° C., 0.19 g of double hydride of lithium aluminium. The mixture is left with stirring for 20 mins. then hydrolysed with an aqueous solution containing 0.95 g of acid sulfate of potassium. 100 ml of ether are added, the aqueous phase is separated and re-extracted with ether.

The organic phases are combined and are washed successively with a 3N hydrochloric acid solution then with a saturated solution of sodium bicarbonate and finally with a saturated solution of sodium chloride.

The product is dried over magnesium sulphate and the solvent is evaporated to dryness.

A colourless oil is obtained.

Yield 96%.

$\alpha_D^{20} = -57.3°$ (c=1% methanol)

This product must be conserved in an argon atmosphere.

NMR spectrum:

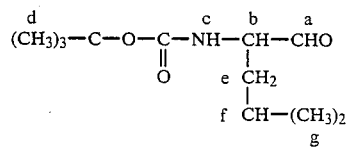

1H at 9.6 ppm ($H_a$, S)-1H at 5.48 ppm ($H_c$, d, $J_{cb}=7$)-1H at 4.2 ppm ($H_b$, m)-3H at 1.9-1.45 ppm ($H_e$, $H_f$, m)-9H at 1.45 ppm ($H_d$, s)-6H at 0.96 ppm ($H_g$, d, $J_{gf}=6.5$).

EXAMPLES 2 TO 6

(a)-By operating as in Example 1(a)-, but by varying the protected L-amino acid used as starting product, the N-methyl N-methoxyamides 2 shown in Table I are obtained.

TABLE I $$\underset{e}{(CH_3)_3}-C-O-\underset{\|}{C}-NH-\underset{R}{CH}-\underset{\|}{C}-\underset{CH_3}{N}-OCH_3 \quad \underset{b}{a}$$

| Example No | R | Yield % | $\alpha_D^{20}$ (1% methanol) | Melting point °C. or NMR spectrum |
|---|---|---|---|---|
| 2a | —CH₃ | 85 | −26.8 | F = 150 |
| 3a | H₃C—CH f<br>  \|<br>g CH₂ h<br>  \|<br>  CH₃ i | 70 | −21.2 | 1H at 5.50 ppm ($H_d$, d, $J_{dc}=9.5$)<br>1H at 4.62 ppm ($H_c$, dd, $J_{cd}=9.5$<br>3H at 3.78 ppm ($H_a$, S) - 3H at 3.<br>ppm ($H_b$, S) - 1H at 1.74 ppm (H<br>9H at 1.42 ppm ($H_e$, S) - 2H at 1<br>1.01 ppm ($H_h$, m) - 3 H at 0.90<br>($H_g$, d, $J_{gf}=7$) - 3 H at 0.88 p<br>($H_i$, t, $J_{ih}=7$) |
| 4a | CH f<br>  \|<br>(CH₃)₂<br>g | 80 | −16 | 1H at 5.21 ppm ($H_d$, d, $J_{dc}=9$)<br>at 4.58 ppm ($H_c$, dd, $J_{cd}=9$, $J_C$<br>3H at 3.78 ppm ($H_a$, S)-3H at 3.2<br>ppm ($H_b$, S)) - 1H at 1.99 ppm<br>m, $J_{fc}=7$) - 9H at 1.44 ppm (H<br>3H at 0.96 ppm ($H_g$, d, $J_{gf}=7$)<br>3H at 0.91 ppm ($H_g$, d, $J_{gf}=7$) |
| 5a | CH₂ ff'<br>  \|<br>  [phenyl]<br>  g | 95 | +2.6 | 5H at 7.6 ppm ($H_g$, m) - 1H at 5<br>ppm ($H_d$, d, $J_{dc}=8.5$) - 1H at<br>ppm ($H_c$, ddd, $J_{cd}=8.5$, $J_{cf}=J_c$<br>3H at 3.60 ppm ($H_a$, S) - 3H at<br>ppm $J_{fc}=6$, $J_{ff}=13.5$) - 1H at 2.8<br>($H_f$, dd, $J_{fc}=6$, $J_{ff}=13.5$)<br>1.38 ppm ($H_e$, S) |

TABLE I-continued $$\underset{e}{(CH_3)_3}-C-O-\underset{\underset{O}{\parallel}}{C}-NH-\underset{\underset{R}{|}}{\overset{d}{C}H}-\underset{\underset{O}{\parallel}}{\overset{c}{C}}-N-\underset{\underset{b}{CH_3}}{\overset{a}{OCH_3}}$$

| Example No | R | Yield % | $\alpha_D^{20}$ (1% methanol) | Melting point °C. or NMR spectrum |
|---|---|---|---|---|
| 6a | f CH—CH₃ g<br>    O<br>    \|<br>    CH₂ hh'<br>    \|<br>    C₆H₅ i | 95 | −20.8 | 5H at 7.3 ppm ($H_i$, m) - 1H at 5.5 ppm ($H_d$, d, $J_{dc}$=9) - 1H at 4.62 ppm ($H_c$, dd, $J_{cd}$=9, $J_{cf}$=3) - 1H 4.54 ppm ($H_h$, d, $J_{hh'}$=12) - 1H 4.40 ppm ($H_{h'}$, d, $J_{hh'}$=12)-1H at 3.89 ppm ($H_f$, dq, $J_{fc}$=3, $J_{fg}$=6. 3H at 3.63 ppm ($H_a$, S) - 3H at 3. ppm ($H_b$, S) 9H at 1.44 ppm ($H_e$, 3H at 1.24 ppm ($H_g$, d, $J_{gf}$=6.5) | b - From the amides shown in Table I, by operating as in Example 1b-, the corresponding amino aldehydes 3 shown in Table II are obtained.

TABLE II $$\underset{d}{(CH_3)_3C}-O-\underset{\underset{O}{\parallel}}{\overset{c}{C}}-NH-\underset{\underset{R}{|}}{\overset{b}{C}H}-\overset{a}{CHO}$$

| Example N° | R | Yield % | $\alpha_D^{20}$ (1% methanol) | Melting point °C. or NMR spectrum |
|---|---|---|---|---|
| 2b | —CH₃ (note 1) | 88 | −34.1 | F = 88–9 |
| 3b | e HC—CH₃ f<br>    \|<br>    CH₂ g<br>    \|<br>    CH₃ h | | | 1H at 9.68 ppm ($H_a$, S) - 1 H at 5.34 ppm ($H_c$, d, $J_{cb}$=7) - 1H 4.28 ppm ($H_b$, dd, $J_{bc}$=7, $J_{be}$= 1H at 2.12–1.92 ppm ($H_e$, m) - 1.42 ppm ($H_d$, S) - 2 H at 1.20 ppm ($H_g$, m) - 3H at 0.99 ppm ( d, $J_{fe}$=7) - 3H at 0.95 ppm ($H_h$ $J_{hg}$=7) |
| 4b | CH e<br>\|<br>(CH₃)₂ f | 93 | −19 | 1H at 9.66 ppm ($H_a$, S) - 1H at 5.33 ppm ($H_c$, d, $J_{cb}$=7) - 1H at 4.23 ppm ($H_b$, dd, $J_{bc}$=7)-1H at 2.29 ppm ($H_e$, m) - 9H at 1.46 ppm ($H_d$, S) - 6H at 0.99 ppm ($H_f$, 2d, $J_{fe}$=7) |
| 5b | CH₂—C₆H₅ | 86 | −44.4 | F = 86 |
| 6b | e HC—CH₃ f<br>    O<br>    \|<br>    CH₂ g<br>    \|<br>    C₆H₅ h | 95 | +16 | 1H at 9.60 ppm ($H_a$, S) - 5H at 7.31 ppm ($H_h$, m) - 1H at 5.40 ppm ($H_c$, d, $J_{cb}$=7.5) - 1H at 4.57 ppm ($H_g$, d, $J_{gg'}$=11.5) - 1H at 4.40 ppm ($H_{g'}$, d, $J_{g'g}$=11 2H at 4.25 ppm ($H_b$, $H_e$, m) - 9H at 1.46 ppm ($H_d$, S) - 3H at 1.25 ppm ($H_f$, d, $J_{fe}$=6.5) |

Note 1 - Due to the low solubility of the starting amide, reduction is in this case effected in tetrahydrofuran instead of ether.

The α alkyl amino aldehydes thus prepared are in particular interesting intermediates of synthesis for the preparation of peptide compounds endowed with therapeutical properties.

What is claimed is:

1. A process for preparing alpha alkyl amino aldehydes of formula:

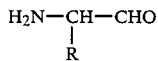

in which R is a straight or branched alkyl group or an aralkyl group which may be substituted by at least one hydroxy, thiol or NHR' group, R' being H or an alkyl group, which process comprises the steps of reacting an activated ester of an amino acid of formula:

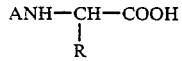

in which the amine functions have been reversibly blocked by a blocking group A, with N,O-dimethyl hydroxylamine in a basic medium to obtain a product of formula:

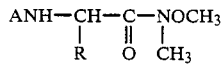

and reducing the product thus obtained by a reduction reaction using a hydride.

2. The process of claim 1, wherein the reaction with N,O-dimethyl hydroxylamine is carried out in solution in a solvent which is methylene chloride or ethyl acetate.

3. The process of claim 1, wherein any blocking group present in the final product is removed at a low temperature in a solvent.

4. The process of claim 2, wherein any blocking group present is removed at a low temperature in a solvent.

5. The process of claim 3, wherein the temperature is about 0° C. and the solvent is ether or tetrahydrofuran.

6. The process of claim 1, wherein the hydride is a double hydride of lithium-aluminum.

7. The process of claim 1, wherein R is the side chain of a natural occurring α-amino acid.

8. The process of claim 7, wherein the α-amino acid is leucine.

9. The process of claim 1, wherein R is

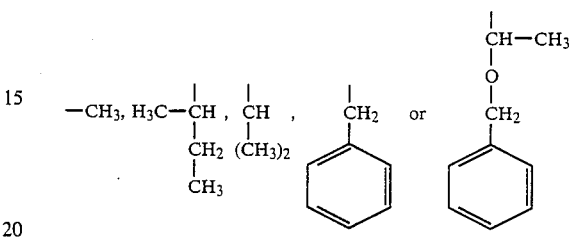

10. The process of claim 9 wherein the hydride is a double hydride of lithium-aluminum, the reaction with the N,O-dimethyl hydroxylamine is carried out in solution with a solvent which is methylene chloride or ethyl acetate and any blocking groups present in the product obtained are removed at a low temperature of about 0° C. in a solvent which is ether or tetrahydrofuran.

11. The process of claim 1 wherein the produced alpha alkyl amino aldehydes have a high rotatory power.

12. The process of claim 9, wherein R is

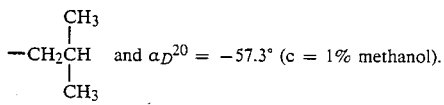

* * * * *